(12) United States Patent
Palucki et al.

(10) Patent No.: US 6,472,398 B1
(45) Date of Patent: Oct. 29, 2002

(54) SPIROPIPERIDINE DERIVATIVES AS MELANOCORTIN RECEPTOR AGONISTS

(75) Inventors: Brenda L. Palucki, Hillsborough, NJ (US); Ravi P. Nargund, East Brunswick, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/812,339

(22) Filed: Mar. 20, 2001

Related U.S. Application Data

(60) Provisional application No. 60/191,669, filed on Mar. 23, 2000.

(51) Int. Cl.[7] ............... A61K 31/496; C07D 471/10
(52) U.S. Cl. ............... 514/253.09; 544/230; 544/6; 544/70; 514/227.8; 514/228.2; 514/228.5; 514/235.2; 514/237.2
(58) Field of Search ............... 544/230; 514/253.09

(56) References Cited

U.S. PATENT DOCUMENTS

| | | |
|---|---|---|
| 5,492,920 A | 2/1996 | Chen et al. |
| 5,536,716 A | 7/1996 | Chen et al. |
| 5,721,251 A | 2/1998 | Chen et al. |
| 5,767,118 A | 6/1998 | Nargund et al. |

FOREIGN PATENT DOCUMENTS

| | | |
|---|---|---|
| WO | WO 97/34604 | 9/1997 |
| WO | WO 98/10653 | 3/1998 |
| WO | WO 99/64002 | 12/1999 |
| WO | WO 00/74679 A1 | 12/2000 |

*Primary Examiner*—Emily Bernhardt
(74) *Attorney, Agent, or Firm*—Philippe L. Durette; Melvin Winokur

(57) ABSTRACT

Certain novel spiropiperidine derivatives of structural formula Ia wherein the substituents are as defined herein are agonists of the human melanocortin receptor(s) and, in particular, are selective agonists of the human melanocortin-4 receptor (MC-4R). They are therefore useful for the treatment, control, or prevention of diseases and disorders responsive to the activation of MC-4R, such as obesity, diabetes, sexual dysfunction, including erectile dysfunction and female sexual dysfunction.

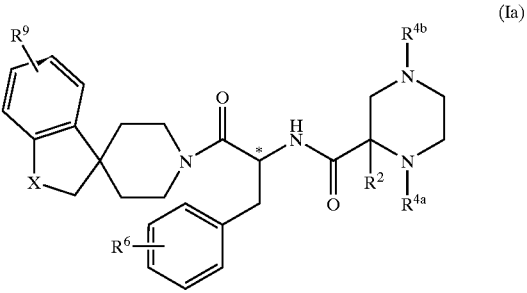

(Ia)

11 Claims, No Drawings

SPIROPIPERIDINE DERIVATIVES AS MELANOCORTIN RECEPTOR AGONISTS

CROSS-REFERENCE TO RELATED APPLICATIONS

The present invention is related to U.S. provisional application Serial No. 60/191,669, filed Mar. 23, 2000, the contents of which are hereby incorporated by reference in their entirety.

FIELD OF THE INVENTION

The present invention relates to spiropiperidine derivatives, their synthesis, and their use as melanocortin receptor (MC-R) agonists. More particularly, the compounds of the present invention are selective agonists of the melanocortin-4 receptor (MC-4R) and are thereby useful for the treatment of disorders responsive to the activation of MC-4R, such as obesity, diabetes, and male and/or female sexual dysfunction.

BACKGROUND OF THE INVENTION

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S.Q. Giraudo et al., "Feeding effects of hypothalamic injection of melanocortin-4 receptor ligands," Brain Research, 80: 302–306 (1998)).

Evidence for the involvement of MC-R's in obesity includes: i) the agouti ($A^{vy}$) mouse which ectopically expresses an antagonist of the MC-1R, MC-3R and -4R is obese, indicating that blocking the action of these three MC-R's can lead to hyperphagia and metabolic disorders; ii) MC-4R knockout mice (D. Huszar et al., Cell, 88: 131–141 (1997)) recapitulate the phenotype of the agouti mouse and these mice are obese; iii) the cyclic heptapeptide MT-II (a non-selective MC-1R, -3R, 4R, and -5R agonist) injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R, and -5R and to attenuate food intake and body weight gain over a 12-week period (I. Corcos et al., "HP228 is a potent agonist of melanocortin receptor-4 and significantly attenuates obesity and diabetes in Zucker fatty rats," Society for Neuroscience abstracts, 23: 673 (1997)).

Five distinct MC-R's have thus far been identified, and these are expressed in different tissues. MC-1R was initially characterized by dominant gain of function mutations at the Extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin-4 receptor (HS014) increases food intake in free-feeding rats," Biochem. Biophys. Res. Commun., 245: 90–93 (1998)). MC-5R is expressed in many tissues, including white fat, placenta and exocrine glands. A low level of expression is also observed in the brain. MC-5R knockout mice reveal reduced sebaceous gland lipid production (Chen et al., Cell, 91: 789–798 (1997)).

Erectile dysfunction denotes the medical condition of inability to achieve penile erection sufficient for successful sexual intercourse. The term "impotence" is oftentimes employed to describe this prevalent condition. Approximately 140 million men worldwide, and, according to a National Institutes of Health study, about 30 million American men suffer from impotency or erectile dysfunction. It has been estimated that the latter number could rise to 47 million men by the year 2000. Erectile dysfunction can arise from either organic or psychogenic causes, with about 20% of such cases being purely psychogenic in origin. Erectile dysfunction increases from 40% at age 40, to 67% at age 75, with over 75% occurring in men over the age of 50. In spite of the frequent occurrence of this condition, only a small number of patients have received treatment because existing treatment alternatives, such as injection therapies, penile prosthesis implantation, and vacuum pumps, have been uniformly disagreeable [for a discussion, see "ABC of sexual health—erectile dysfunction," Brit. Med. J. 318: 387–390 (1999)]. Only more recently have more viable treatment modalities become available, in particular orally active agents, such as sildenafil citrate, marketed by Pfizer under the brand name of Viagra®. Sildenafil is a selective inhibitor of type V phosphodiesterase (PDE-V), a cyclic-GMP-specific phosphodiesterase isozyme [see R. B. Moreland et al., "Sildenafil: A Novel Inhibitor of Phosphodiesterase Type 5 in Human Corpus Cavernosum Smooth Muscle Cells," Life Sci., 62: 309–318 (1998)]. Prior to the introduction of Viagra on the market, less than 10% of patients suffering from erectile dysfunction received treatment. Sildenafil is also being evaluated in the clinic for the treatment of female sexual dysfunction.

The regulatory approval of Viagra® for the oral treatment of erectile dysfunction has invigorated efforts to discover even more effective methods to treat erectile dysfunction. Several additional selective PDE-V inhibitors are in clinical trials. UK-114542 is a sildenafil backup from Pfizer with supposedly improved properties. IC-351 (ICOS Corp.) is claimed to have greater selectivity for PDE-V over PDE-VI than sildenafil. Other PDE-V inhibitors include M-54033 and M-54018 from Mochida Pharmaceutical Co. and E-4010 from Eisai Co., Ltd.

Other pharmacological approaches to the treatment of erectile dysfunction have been described [see, e.g., "Latest Findings on the Diagnosis and Treatment of Erectile Dysfunction," Drug News & Perspectives, 9: 572–575 (1996); "Oral Pharmacotherapy in Erectile Dysfunction," Current Opinion in Urology, 7: 349–353 (1997)]. A product under clinical development by Zonagen is an oral formulation of the alpha-adrenoceptor antagonist phentolamine mesylate under the brand name of Vasomax®. Vasomax® is also being evaluated for the treatment of female sexual dysfunction.

Drugs to treat erectile dysfunction act either peripherally or centrally. They are also classified according to whether they "initiate" a sexual response or "facilitate" a sexual response to prior stimulation [for a discussion, see "A Therapeutic Taxonomy of Treatments for Erectile Dysfunction: An Evolutionary Imperative," *Int. J. Impotence Res.,* 9: 115–121 (1997)]. While sildenafil and phentolamine act peripherally and are considered to be "enhancers" or "facilitators" of the sexual response to erotic stimulation, sildenafil appears to be efficacious in both mild organic and psychogenic erectile dysfunction. Sildenafil has an onset of action of 30–60 minutes after an oral dose with the effect lasting about 4 hours, whereas phentolamine requires 5–30 minutes for onset with a duration of 2 hours. Although sildenafil is effective in a majority of patients, it takes a relatively long time for the compound to show the desired effects. The faster-acting phentolamine appears to be less effective and to have a shorter duration of action than sildenafil. Oral sildenafil is effective in about 70% of men who take it, whereas an adequate response with phentolamine is observed in only 35–40% of patients. Both compounds require erotic stimulation for efficacy. Since sildenafil indirectly increases blood flow in the systemic circulation by enhancing the smooth muscle relaxation effects of nitric oxide, it is contraindicated for patients with unstable heart conditions or cardiovascular disease, in particular patients taking nitrates, such as nitroglycerin, to treat angina. Other adverse effects associated with the clinical use of sildenafil include headache, flushing, dyspepsia, and "abnormal vision," the latter the result of inhibition of the type VI phosphodiesterase isozyme (PDE-VI), a cyclic-GMP-specific phosphodiesterase that is concentrated in the retina. "Abnormal vision" is defined as a mild and transient "bluish" tinge to vision, but also an increased sensitivity to light or blurred vision.

Synthetic melanocortin receptor agonists (melanotropic peptides) have been found to initiate erections in men with psychogenic erectile dysfunction [See H. Wessells et al., "Synthetic Melanotropic Peptide Initiates Erections in Men With Psychogenic Erectile Dysfunction: Double-Blind, Placebo Controlled Crossover Study," *J. Urol.,* 160: 389–393 (1998); *Fifteenth American Peptide Symposium,* Jun. 14–19, 1997 (Nashville Tenn.)]. Activation of melanocortin receptors of the brain appears to cause normal stimulation of sexual arousal. In the above study, the centrally acting α-melanocyte-stimulating hormone analog, melanotan-II (MT-II), exhibited a 75% response rate, similar to results obtained with apomorphine, when injected intramuscularly or subcutaneously to males with psychogenic erectile dysfunction. MT-II is a synthetic cyclic heptapeptide, Ac-Nle-c[Asp-His-DPhe-Arg-Trp-Lys]-NH$_2$, which contains the 4–10 melanocortin receptor binding region common to α-MSH and adrenocorticotropin, but with a lactam bridge. It is a non-selective MC-1R, -3R, -4R, and -5R agonist (Dorr et al., *Life Sciences,* Vol. 58, 1777–1784, 1996). MT-II (also referred to as PT-14) (Erectide®) is presently in clinical development by Palatin Technologies, Inc. and TheraTech, Inc. as a non-penile subcutaneous injection formulation. It is considered to be an "initiator" of the sexual response. The time to onset of erection with this drug is relatively short (10–20 minutes) with a duration of action approximately 2.5 hours. Adverse reactions observed with MT-II include nausea, flushing, loss of appetite, stretching, and yawning and may be the result of activation of MC-1R, MC-2R, MC-3R, and/or MC-5R. MT-II must be administered parenterally, such as by subcutaneous, intravenous, or intramuscular route, since it is not absorbed into the systemic circulation when given by the oral route. Compositions of melanotropic peptides and methods for the treatment of psychogenic erectile dysfunction are disclosed in U.S. Pat. No. 5,576,290, assigned to Competitive Technologies.

Because of the unresolved deficiencies of the various pharmacological agents discussed above, there is a continuing need in the medical arts for improved methods and compositions to treat individuals suffering from psychogenic and/or organic erectile dysfunction. Such methods and compositions should have wider applicability, enhanced convenience and ease of compliance, short onset of action, reasonably long duration of action, and minimal side effects with few contraindications, as compared to agents now available.

WO 99/64002 (published Dec. 16, 1999) discloses spiropiperidine derivatives as melanocortin receptor agonists which are useful for the treatment of obesity, diabetes mellitus, and sexual dysfunction.

It is therefore an object of the present invention to provide novel spiropiperidine derivatives which are useful as melanocortin receptor agonists.

It is another object of the present invention to provide novel spiropiperidine derivatives which are selective agonists of the melanocortin-4 (MC-4R) receptor.

It is another object of the present invention to provide pharmaceutical compositions comprising melanocortin receptor agonists.

It is another object of the present invention to provide methods for the treatment or prevention of disorders, diseases, or conditions responsive to the activation of the melanocortin receptor in a mammal in need thereof by administering the compounds and pharmaceutical compositions of the present invention.

It is another object of the present invention to provide compounds and pharmaceutical compositions useful for the treatment or prevention of obesity, diabetes mellitus, and male and/or female sexual dysfunction.

It is another object of the present invention to provide compounds and pharmaceutical compositions for the treatment or prevention of erectile dysfunction.

It is another object of the present invention to provide methods for the treatment or prevention of obesity, diabetes mellitus, and male and/or female sexual dysfunction.

These and other objects will become readily apparent from the detailed description that follows.

SUMMARY OF THE INVENTION

The present invention relates to novel spiropiperidine derivatives of structural formula (I):

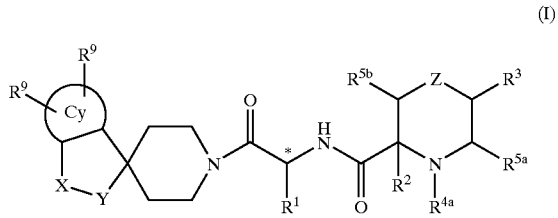

These spiropiperidine derivatives are effective as melanocortin receptor agonists and are particularly effective as selective melanocortin-4 receptor (MC-4R) agonists. They are therefore useful for the treatment and/or prevention of disorders responsive to the activation of MC-4R, such as obesity, diabetes as well as male and/or female sexual dysfunction, in particular, male erectile dysfunction.

The present invention also relates to pharmaceutical compositions comprising the compounds of the present invention and a pharmaceutically acceptable carrier.

The present invention also relates to methods for the treatment or prevention of disorders, diseases, or conditions responsive to the activation of the melanocortin receptor in a mammal in need thereof by administering the compounds and pharmaceutical compositions of the present invention.

The present invention also relates to methods for the treatment or prevention of obesity, diabetes mellitus, and male and/or female sexual dysfunction by administering the compounds and pharmaceutical compositions of the present invention.

The present invention also relates to methods for treating erectile dysfunction by administering the compounds and pharmaceutical compositions of the present invention.

DETAILED DESCRIPTION OF THE INVENTION

The present invention provides novel spiropiperidine derivatives of structural formula (I) or pharmaceutically acceptable salts thereof which are useful as melanocortin receptor agonists:

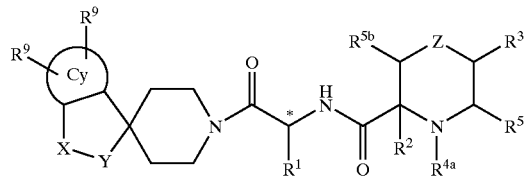

(I)

wherein

Z is O, S, or $NR^{4b}$;

n is 0, 1, or 2;

r is 1, 2, or 3;

X is $CHCO_2R^3$, $CHC(O)N(R^3)_2$, $NSO_2R^8$, $CHN(R^3)COR^8$, $CHN(R^3)SO_2R^8$, $CHCH_2OR^3$, or $CHCH_2heteroaryl$;

Y is $(CH_2)_r$, $CHC_{1-8}$ alkyl, O, C=O, or $SO_2$, with the proviso that when Y is O, the ring atom X is carbon;

Cy is benzene, pyridine, or cyclohexane;

$R^1$ is selected from the group consisting of
hydrogen,
$C_{1-8}$ alkyl,
$(CHR^7)_n$—$C_{3-6}$ cycloalkyl,
$(CHR^7)_n$—$O(CHR^7)$aryl,
$(CHR^7)_n$aryl, and
$(CHR^7)_n$heteroaryl;
in which aryl and heteroaryl are unsubstituted or substituted with one to three groups independently selected from $R^6$; and alkyl and cycloalkyl are unsubstituted or substituted with one to three groups independently selected from $R^6$ and oxo;

$R^2$ is selected from the group consisting of
hydrogen,
$C_{1-8}$ alkyl,
$(CH_2)_nC_{3-6}$ cycloalkyl, and
$(CH_2)_n$-aryl;

$R^3$ is selected from the group consisting of
hydrogen,
$C_{1-8}$ alkyl,
$(CH_2)_n$-aryl,
$(CH_2)_nC_{3-6}$ cycloalkyl,
$(CH_2)_n$-heteroaryl, and
$(CH_2)_n$-heterocyclyl;
in which aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo;

or $R^3$ and $R^{5a}$ and the carbons to which they are attached form a 5- to 7-membered ring optionally containing an additional heteroatom selected from O, S, and $NR^7$;

or $R^3$ and $R^{4b}$ and the carbons to which they are attached form a 5- to 7-membered ring optionally containing an additional heteroatom selected from O, S, and NR7;

$R^{4a}$ and $R^{4b}$ are each independently selected from the group consisting of
hydrogen,
amidino,
$C_{1-8}$ alkyl,
$(CH_2)_n$-aryl,
$(CH_2)_nC_{3-6}$ cycloalkyl,
$(CH_2)_n$-heteroaryl,
$(CH_2)_n$-heterocyclyl,
$CO(CH_2)_{0-1}C(R^7)_2NH_2$,
$COC(R^7)_2NHCO_2R^7$,
$COR^7$,
$(CH_2)_nOR^7$,
$(CH_2)_nCO_2R^7$,
$CH_2C\equiv CH$,
$CH_2CHF_2$,
$CONR^7R^7$,
$SO_2R^7$, and
$SO_2NR^7R^7$;
in which aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo;

or $R^{4a}$ and $R^2$ and the carbons to which they are attached form a 5- to 7-membered ring optionally containing an additional heteroatom selected from O, S. and $NR^7$; or $R^{4a}$ and $R^{4b}$ and the atoms to which they are attached form a 5- to 7-membered ring;

$R^{5a}$ and $R^{5b}$ are each independently selected from the group consisting of
hydrogen,
$C_{1-8}$ alkyl, and
$C_{3-8}$ cycloalkyl;
wherein alkyl and cycloalkyl are unsubstituted or substituted with one to three groups independently selected from $R^6$ and oxo;

or $R^{5a}$ and $R^{5b}$ together with the carbons to which they are attached form a 5- to 7-membered ring;

$R^6$ is selected from the group consisting of
hydrogen
$C_{1-8}$ alkyl,
$(CH_2)_n$-aryl,
$(CH_2)_nC_{3-7}$ cycloalkyl,
$(CH_2)_n$-heteroaryl,
halo,
$OR^7$,
$NHSO_2R^7$,
$N(R^7)_2$,
$C\equiv N$,
$CO_2R^7$,
$C(R^7)(R^7)N(R^7)_2$,
$NO_2$,
$SO_2N(R^7)_2$,
$S(O)_{0-2}R^7$, $CF_3$, and
$OCF_3$;

each $R^7$ is independently selected from the group consisting of
hydrogen,
$C_{1-8}$ alkyl,
$(CH_2)_n$-aryl, and
$(CH_2)_n C_{3-7}$ cycloalkyl;

each $R^8$ is independently selected from the group consisting of
hydrogen,
$C_{1-8}$ alkyl,
$(CH_2)_n$-aryl,
$(CH_2)_n$-heteroaryl,
$(CH_2)_n$-heterocyclyl,
$(CH_2)_n C_{3-7}$ cycloalkyl,
$(CH_2)_n N(R^3)_2$,
$(CH_2)_n$NH-heteroaryl, and
$(CH_2)_n$NH-heterocyclyl;
wherein aryl and heteroaryl are unsubstituted or substituted with one to three groups independently selected from $R^6$; and alkyl, cycloalkyl, heterocyclyl, and $(CH_2)_n$ are unsubstituted or substituted with one to three groups independently selected from $R^6$ and oxo;

or two $R^8$ groups together with the atoms to which they are attached form a 5- to 8-membered mono- or bi-cyclic ring system optionally containing an additional heteroatom selected from O, S, $NR^7$, NBoc, and NCbz; and $R^9$ is selected from the group consisting of
hydrogen,
halo,
$C_{1-8}$ alkyl,
$C_{1-6}$ alkoxy,
CN,
$CF_3$, and
$OCF_3$.

In one embodiment of the compounds of the present invention, Cy is benzene or cyclohexane. In a class of this embodiment, Cy is benzene.

In a second embodiment of the compounds of the present invention, $R^1$ is $CHR^7$-aryl, $CHR^7OCHR^7$-aryl, or $CH(R^7)$-heteroaryl wherein aryl and heteroaryl are optionally substituted with one or two $R^6$ groups. In a class of this embodiment, $R^1$ is benzyl optionally substituted with one or two groups selected from halogen, $C_{1-4}$ alkyl, $C_{1-4}$ alkoxy, $CF_3$, and $OCF_3$. In a subclass of this class, $R^1$ is 4-chlorobenzyl, 4-fluorobenzyl, or 4-methoxybenzyl.

In a third embodiment of the compounds of the present invention, Z is $NR^{4b}$.

In a fourth embodiment of the compounds of the present invention, $R^{4a}$ and $R^{4b}$ are each independently selected from the group consisting of hydrogen,
amidino,
$C_{1-8}$ alkyl,
$(CH_2)_n$-aryl,
$(CH_2)_n$-heteroaryl,
$(CH_2)_n$-heterocyclyl,
$(CH_2)_n C_{3-6}$ cycloalkyl,
$(CH_2)_n CO_2 R^7$,
$CONR^7 R^7$,
$COR^7$,
$CO(CH_2)_{0-1}C(R^7)_2NH_2$,
$COC(R^7)_2 NHCO_2 R^7$,
$(CH_2)_n OR^7$,
$CH_2 C\equiv CH$,
$CH_2 CHF_2$,
$SO_2 R_7$, and
$SO_2 NR^7 R^7$;
in which aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo;

or $R^{4a}$ and $R^{4b}$ and the atoms to which they are attached form a 6-membered ring;

$R^3$, $R^{5a}$, and $R^{5b}$ are each independently hydrogen, $C_{1-4}$ alkyl, or aryl, wherein aryl is unsubstituted or substituted with one to three groups independently selected from $R^6$; or $R^3$ and $R^{5a}$ and the carbons to which they are attached form a 6-membered ring optionally containing an additional heteroatom selected from O, S, and $NR^7$; or $R^3$ and $R^{4b}$ and the carbons to which they are attached form a 6-membered ring optionally containing an additional heteroatom selected from O, S, and $NR^7$.

In a class of this embodiment, $R^{4a}$ and $R^{4b}$ are each independently selected from the group consisting of
hydrogen,
amidino,
$C_{1-4}$ alkyl,
$(CH_2)_{0-1}$ aryl
$(CH_2)_{0-1}$-heteroaryl,
$(CH_2)_{0-1}$-heterocyclyl,
$(CH_2)_{0-1}C_{3-6}$ cycloalkyl,
$(CH_2)_{0-1}CO_2 R^7$,
$CO(CH_2)_{0-1}C(Me)_2 NH_2$,
$COC(Me)_2 NHCO_2 R^7$,
$(CH_2)_2 OR^7$,
$COR^7$,
$CONR^7 R^7$,
$SO_2 R^7$, and
$SO_2 NR^7 R^7$;
in which aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo;
$R^3$, $R^{5a}$, and $R^{5b}$ are each independently hydrogen, $C_{1-4}$ alkyl, or phenyl, wherein phenyl is unsubstituted or substituted with one to three groups independently selected from $R^6$; or $R^3$ and $R^{5a}$ and the carbons to which they are attached form a 6-membered ring optionally containing an additional heteroatom selected from O, S, and $NR^7$; or $R^3$ and $R^{4b}$ and the carbons to which they are attached form a 6-membered ring optionally containing an additional heteroatom selected from O, S, and $NR^7$.

In a fifth embodiment of the compounds of the present invention, $R^2$ is H or $CH_3$.

In a further embodiment of the present invention, there are provided compounds of structural formula Ia:

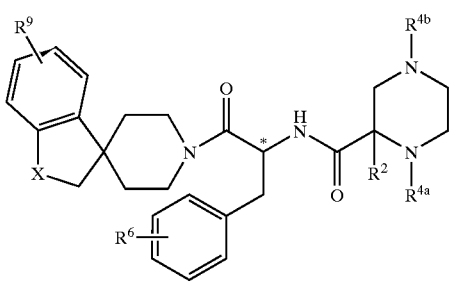

(Ia)

wherein
X is $CHCO_2R^3$, $CHC(O)N(R^3)_2$, $NSO_2R^8$, $CHN(R^3)COR^8$, or $CHN(R^3)SO_2R^8$;
$R^6$ is hydrogen, halo, or methoxy;
$R^2$ is hydrogen or methyl;
$R^9$ is hydrogen or halo; and
$R^{4a}$ and $R^{4b}$ are each independently selected from the group consisting of
hydrogen,
amidino,
$C_{1-4}$ alkyl,
$(CH_2)_{0-1}$ aryl
$(CH_2)_{0-1}$-heteroaryl,
$(CH_2)_{0-1}$-heterocyclyl,
$(CH_2)_{0-1}C_{3-6}$ cycloalkyl,
$CO_2R^7$,
$CO(CH_2)_{0-1}C(Me)_2NH_2$,
$COC(Me)_2NHCO_2R^7$,
$(CH_2)_2OR^7$,
$COR^7$,
$CONR^7R^7$,
$SO_2R^7$, and
$SO_2NR^7R7$;
in which aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo.

In a further embodiment of the present invention, there are provided compounds of structural formula Ia:

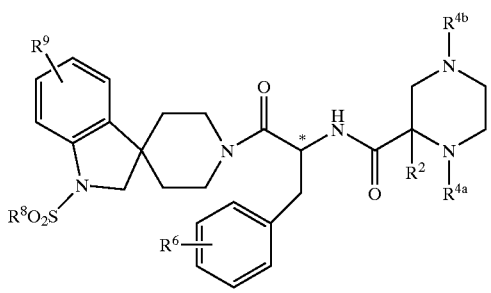

(Ib)

wherein
$R^6$ is hydrogen, halo, or methoxy;
$R^2$ is hydrogen or methyl;
$R^9$ is hydrogen or halo; and
$R^{4a}$ and $R^{4b}$ are each independently selected from the group consisting of
hydrogen,
$C_{1-4}$ alkyl,
$(CH_2)_{0-1}$-aryl
$(CH_2)_{0-1}$-heteroaryl,
$(CH_2)_{0-1}$-heterocyclyl,
$(CH_2)_{0-1}C_{3-6}$ cycloalkyl,
in which aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo.

In yet a further embodiment of compounds of formulae I, Ia, or Ib the carbon atom marked with * has the R configuration.

Illustrative but nonlimiting examples of the present invention are compounds of structural formula Ic shown below that are useful as melanocortin receptor agonists:

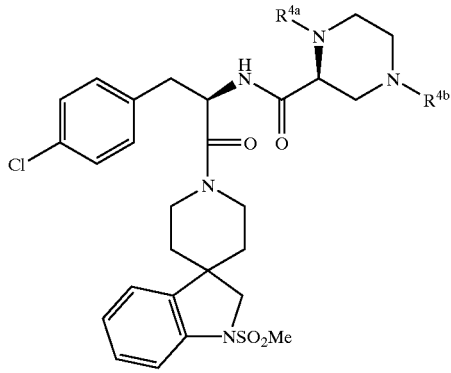

Ib

| Ex. | $R^{4a}$ | $R^{4b}$ |
|---|---|---|
| 1 | H | Ph |
| 2 | Boc | Cbz |
| 3 | Boc | H |
| 4 | Boc | 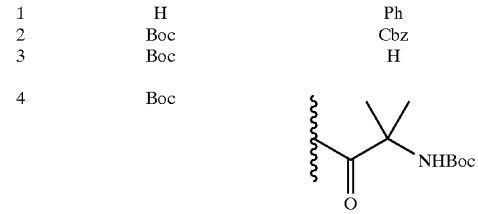 |
| 5 | Boc | 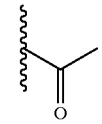 |
| 6 | Boc |  |
| 7 | Boc | 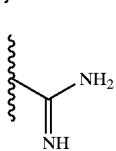 |
| 8 | Boc |  |

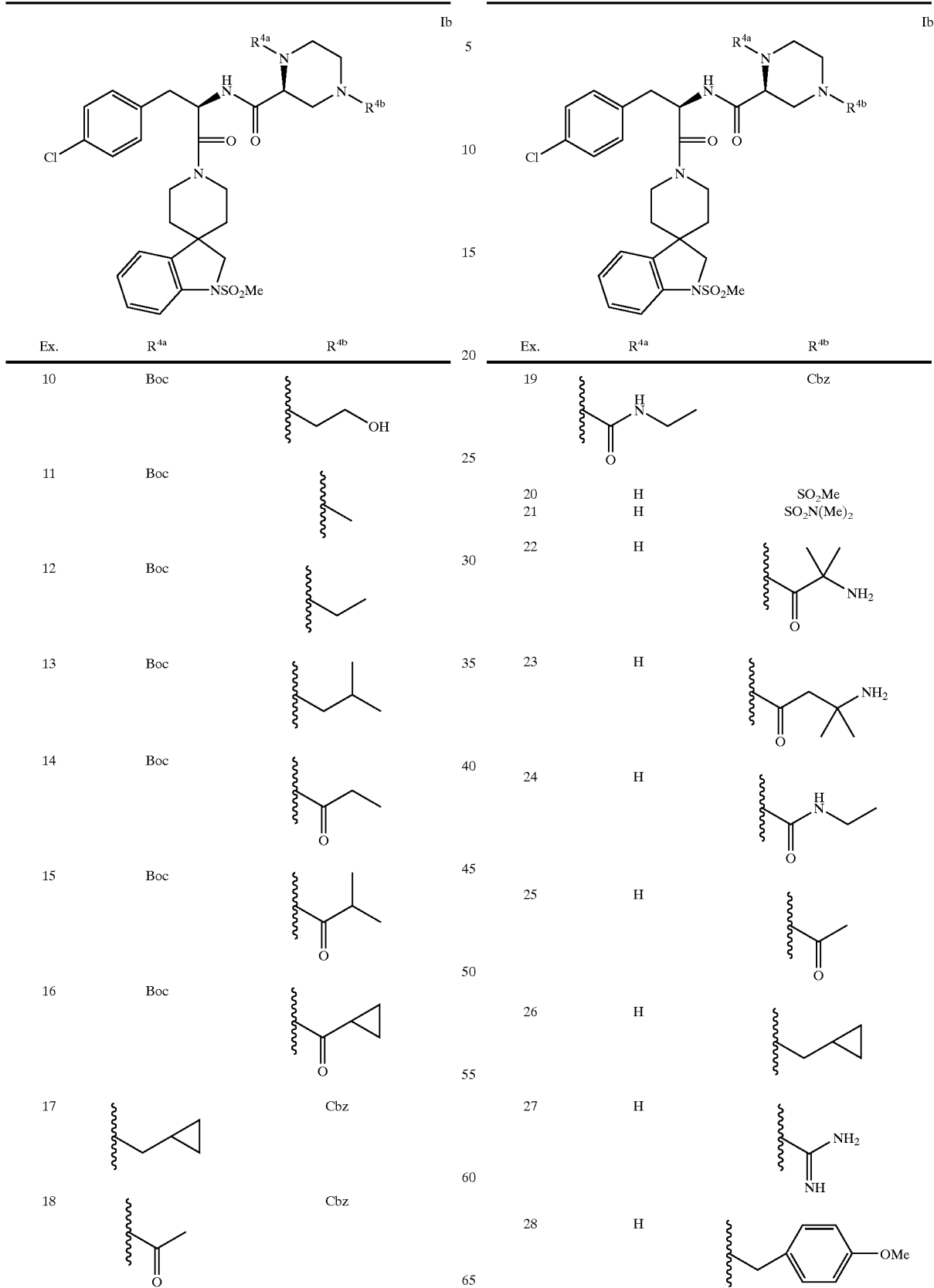

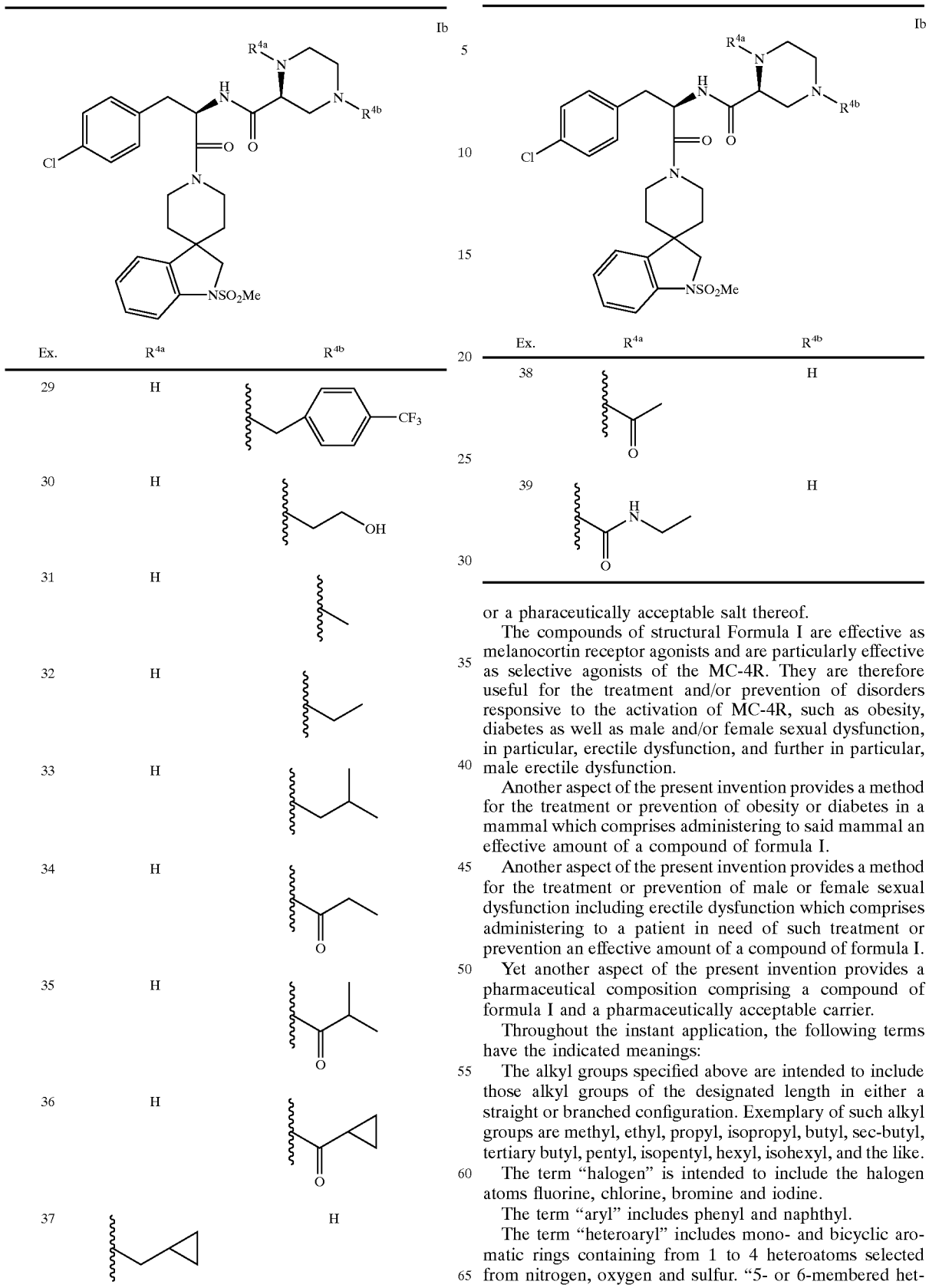

or a pharaceutically acceptable salt thereof.

The compounds of structural Formula I are effective as melanocortin receptor agonists and are particularly effective as selective agonists of the MC-4R. They are therefore useful for the treatment and/or prevention of disorders responsive to the activation of MC-4R, such as obesity, diabetes as well as male and/or female sexual dysfunction, in particular, erectile dysfunction, and further in particular, male erectile dysfunction.

Another aspect of the present invention provides a method for the treatment or prevention of obesity or diabetes in a mammal which comprises administering to said mammal an effective amount of a compound of formula I.

Another aspect of the present invention provides a method for the treatment or prevention of male or female sexual dysfunction including erectile dysfunction which comprises administering to a patient in need of such treatment or prevention an effective amount of a compound of formula I.

Yet another aspect of the present invention provides a pharmaceutical composition comprising a compound of formula I and a pharmaceutically acceptable carrier.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "halogen" is intended to include the halogen atoms fluorine, chlorine, bromine and iodine.

The term "aryl" includes phenyl and naphthyl.

The term "heteroaryl" includes mono- and bicyclic aromatic rings containing from 1 to 4 heteroatoms selected from nitrogen, oxygen and sulfur. "5- or 6-membered heteroaryl" are monocyclic heteroaromatic rings, examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

The term "5- or 6-membered carbocyclyl" is intended to include non-aromatic rings containing only carbon atoms such as cyclopentyl and cyclohexyl.

The term "5 and 6-membered heterocyclyl" is intended to include non-aromatic heterocycles containing one to four heteroatoms selected from nitrogen, oxygen and sulfur. Examples of a 5 or 6-membered heterocyclyl include piperidine, morpholine, thiamorpholine, pyrrolidine, imidazolidine, tetrahydrofuran, piperazine, and the like.

Certain of the above defined terms may occur more than once in the above formula and upon such occurrence each term shall be defined independently of the other; thus for example, $NR^7R^7$ may represent $NH_2$, $NHCH_3$, $N(CH_3)CH_2CH_3$, and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction is often associated with age and is generally caused by a physical disease or as a side-effect of drug treatment.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by another bioactive agent. The "agonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the the present instance, the ability of a compound of formula I to bind to a melanocortin receptor. Binding affinities for the compounds of the present invention were measured in the binding assay described below and are expressed as $IC_{50}$'s. "Efficacy" describes the relative intensity with which agonists vary in the response they produce even when they occupy the same number of receptors and with the same affinity. Efficacy is the property that enables drugs to produce responses. Properties of compounds/drugs can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention at a particular concentration were measured in the functional assay described below.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed with compounds of Formula I.

Compounds of the Formula I may be separated into their individual diastereoisomers by, for example, fractional crystallization from a suitable solvent, for example methanol or ethyl acetate or a mixture thereof, or via chiral chromatography using an optically active stationary phase.

Alternatively, any diastereomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediarine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Formula I are meant to also include the pharmaceutically acceptable salts.

Utility

Compounds of formula I are melanocortin receptor agonists and as such are useful in the treatment, control or prevention of diseases, disorders or conditions responsive to the activation of one or more of the melanocortin receptors including, but are not limited to, MC-1, MC-2, MC-3, MC-4, or MC-5. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immunemodulation, rheumatoid arthritis, skin tanning, acne and other skin disorders, neuroprotective and cognitive and memory enhancement including the treatment of Alzheimer's disease. Some compounds encompassed by formula I show highly selective affinity for the melanocortin-4 receptor relative to MC-1R, MC-2R, MC-3R, and MC-5R, which makes them especially useful in the prevention and treatment of obesity, as well as male and/or female sexual dysfunction, including erectile dysfunction.

"Male sexual dysfunction" includes impotence, loss of libido, and erectile dysfunction.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders.

"Female sexual dysfunction" can be seen as resulting from multiple components including dysfunction in desire, sexual arousal, sexual receptivity, and orgasm related to disturbances in the clitoris, vagina, periurethral glans, and other trigger points of sexual function. In particular, anatomic and functional modification of such trigger points may diminish the orgasmic potential in breast cancer and gynecologic cancer patients. Treatment of female sexual dysfunction with an MC-4 receptor agonist can result in improved blood flow, improved lubrication, improved sensation, facilitation of reaching orgasm, reduction in the refractory period between orgasms, and improvements in arousal and desire. In a broader sense, "female sexual dysfunction" also incorporates sexual pain, premature labor, and dysmenorrhea.

Administration and Dose Ranges

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally or topically.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of the present invention are administered at a daily dosage of from about 0.001 milligram to about 100 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

For the treatment of sexual dysfunction compounds of the present invention are given in a dose range of 0.001 milligram to about 100 milligram per kilogram of body weight, preferably as a single dose orally or as a nasal spray.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas, such as tolbutamide and glipizide;

(d) α-glucosidase inhibitors (such as acarbose),
(e) cholesterol lowering agents such as (i) HMG-CoA reductase inhibitors (lovastatin, simvastatin, pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption for example beta-sitosterol and (acyl CoA:cholesterol acyltransferase) inhibitors for example melinamide, (v) probucol, (vi) vitamin E, and (vii) thyromimetics;
(f) PPARδ agonists, such as those disclosed in WO97/28149;
(g) antiobesity compounds, such as fenfluramine, dexfenfluramine, phentermine, sibutramine, orlistat, or $β_3$ adrenergic receptor agonists;
(h) feeding behavior modifying agents, such as neuropeptide Y antagonists (e.g. neuropeptide Y5) such as those disclosed in WO 97/19682, WO 97/20820, WO 97/20821, WO 97/20822 and WO 97/20823;
(i) PPARα agonists such as described in WO 97/36579 by Glaxo;
(j) PPARγ antagonists as described in WO97/10813;
(k) serotonin reuptake inhibitors such as fluoxetine and sertraline;
(l) growth hormone secretagogues such as MK-0677; and
(m) agents useful in the treatment of male and/or female sexual dysfunction, such as type V cyclic-GMP-specific phosphodiesterase (PDE-V) inhibitors, including sildenafil and IC-351; alpha-adrenergic receptor antagonists, including phentolamine and yohimbine and pharmaceutically acceptable salts thereof; and dopamine receptor agonists, such as apomorphine.

In one embodiment of a combination for the treatment of male or female sexual dysfunction, the second ingredient to be combined with a compound of Formula I can be a type V cyclic-GMP-specific phosphodiesterase (PDE-V) inhibitor, such as sildenafil and IC-351 or a pharmaceutically acceptable salt thereof; an alpha-adrenergic receptor antagonist, such as phentolamine and yohimbine or a pharmaceutically acceptable salt thereof; or a dopamine receptor agonist, such as apomorphine or a pharmaceutically acceptable salt thereof.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

In the Schemes and Examples below, various reagent symbols and abbreviations have the following meanings:

| | |
|---|---|
| BINAP | 2,2'-Bis(diphenylphosphino)-1,1'-binaphthyl |
| BOC | t-butyloxycarbonyl |
| Bu | butyl |
| calc. | calculated |
| CBZ | benzyloxycarbonyl |
| DEAD | diethyl azodicarboxylate |
| DIEA | diisopropylethylamine |
| DMAP | 4-dimethylamino-pyridine |
| DMF | N,N-dimethylformamide |
| EDC | 1-(3-dimethylaminopropyl)3-ethylcarbodiimide HCl |
| eq. | equivalent(s) |
| ESI-MS | electron spray ion-mass spectroscopy |
| Et | ethyl |
| EtOAc | ethyl acetate |
| HOAt | 1-hydroxy-7-azabenzotriazole |
| HOBt | 1-hydroxybenzotriazole hydrate |
| HPLC | high performance liquid chromatography |
| LDA | lithium diisopropylamide |
| MC-xR | melanocortin receptor (x being a number) |
| Me | methyl |
| MF | molecular formula |
| Ms | methanesulfonyl |
| NMM | N-methylmorpholine |
| $Pd_2(dba)_2$ | Tris(dibenzylideneacetone)dipalladium(0) |
| Ph | phenyl |
| Phe | phenylalanine |
| Pr | propyl |
| prep. | prepared |
| PyBrop | bromo-tris-pyrrolidino-phosphonium hexafluorophosphate |
| TFA | trifluoroacetic acid |
| THF | tetrahydrofuran |
| Tic | 1,2,3,4-tetrahydroisoquinoline-3-carboxylic acid |
| TLC | thin-layer chromatography |

Preparation of Compounds of the Invention

The novel compounds of the present invention can be prepared according to the procedure of the following schemes and examples, using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

The following Schemes and Examples describe procedures for making representative compounds of the present invention. Moreover, by utilizing the procedures and intermediates described in detail in PCT International Application Publication No. WO 99/64002 (Dec. 16, 1999), PCT International Application Publication No. WO 00/74679 (Dec. 14, 2000), and U.S. Pat. No. 5,536,716, the contents of all of which are incorporated by reference herein in their entirety, in conjunction with the disclosure contained herein, one of ordinary skill in the art can readily prepare additional compounds of the present invention claimed herein.

The phrase "standard peptide coupling reaction conditions" means coupling a carboxylic acid with an amine using an acid activating agent such as EDC, DCC, and BOP in a inert solvent such as dichloromethane in the presence of a catalyst such as HOBT. The use of protecting groups for amine and carboxylic acid to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation with hydrogen in the presence of a noble metal or its oxide such as palladium on activated carbon in a protic solvent such as ethanol. In cases where catalytic hydrogenation is contraindicated due to the presence of other potentially reactive functionality, removal of CBZ groups can also be achieved by treatment with a solution of hydrogen bromide in acetic acid, or by treatment with a mixture of TFA and dimethylsulfide. Removal of BOC protecting groups is carried out in a solvent such as methylene chloride or methanol or ethyl acetate, with a strong acid, such as trifluoroacetic acid or hydrochloric acid or hydrogen chloride gas.

It is understood that in some cases the order of carrying out the reaction schemes below may be varied to facilitate the reaction or to avoid unwanted reaction products.

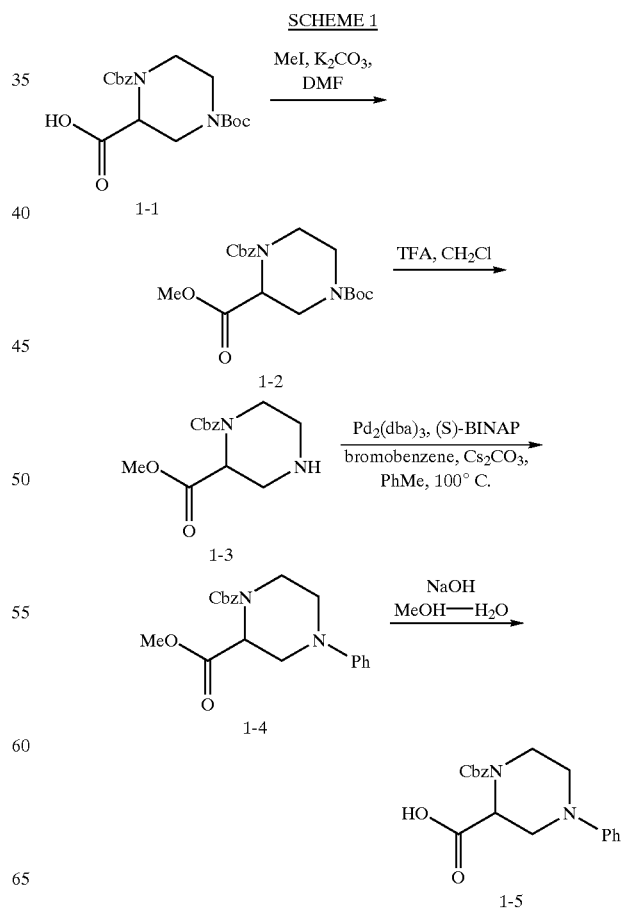

SCHEME 1

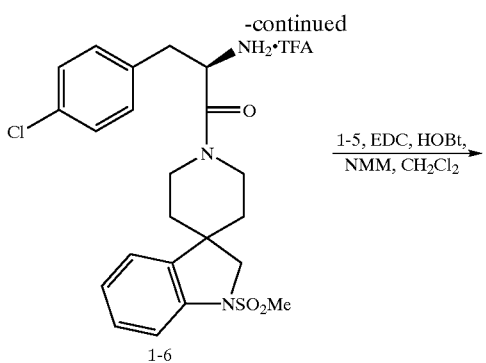

1-6

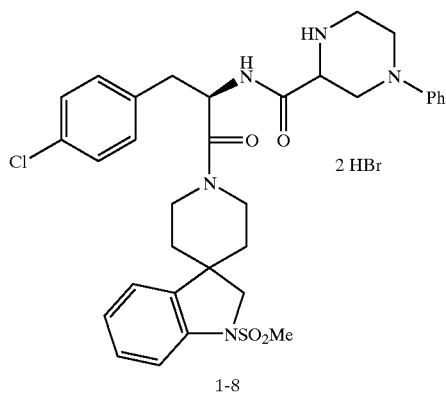

1-7

1-8

EXAMPLE 1

Step A

A 25-mL, round-bottomed flask was purged under nitrogen and charged with 1-(benzyloxycarbonyl)-4-(tert-butoxycarbonyl)piperazine-2-carboxylic acid (1-1) (0.456 g, 1.25 mmol) (the preparation of 1-1 from commercially available piperazine-2-carboxylic acid was achieved via modifications to the procedure described by Bigge and coworkers in *Tetrahedron Lett.* 1989, 30, 5193) and 6.5 mL of DMF. Potassium carbonate (0.207 g, 1.50 mmol) was then added followed by the addition of methyl iodide (0.40 mL, 6.26 mmol), and the resulting mixture was stirred at room temperature for 23 h. The cloudy yellow mixture was diluted with EtOAc and water, and the layers were separated. The organic phase was washed with water and brine, dried over $Na_2SO_4$, filtered, and concentrated to give a yellow oil. Purification by column chromatography (50% ethyl acetate-hexane) provided 1-2 (0.551 g) as a slightly yellow oil.

Step B

Compound 1-2 (0.300 g, 0.793 mmol) was dissolved in 2 mL of methylene chloride and 2 mL of trifluoroacetic acid, and this solution was stirred at room temperature for 45 min. The mixture was then concentrated with toluene twice to give a yellow oil. The oil was dissolved in EtOAc and washed with 1N NaOH solution, and the aqueous layer was extracted with EtOAc. The combined organic phases were dried over $K_2CO_3$, filtered, and concentrated to give 1-3 as a clear oil.

Step C

An oven dried Pyrex tube (ca. 25 mL capacity) with a side arm equipped with an nitrogen inlet adapter was charged with freshly ground cesium carbonate (0.362 g, 1.11 mmol), $Pd_2(dba)_3$ (0.011 g, 0.012 mmol), and (S)-BINAP (0.022 g, 0.036 mmol), and then purged under nitrogen. A solution of piperazine 1-3 (0.793 mmol) in 3 mL of toluene was then added via cannula followed by the addition of bromobenzene (0.10 mL, 0.950 mmol) via syringe. The orange-brown mixture was placed in a 100° C. oil bath and stirred for 26 h. The resulting cloudy orange mixture was filtered through a pad of Celite using ethyl acetate, and the filtrate was concentrated. Column chromatography on 10 g of silica gel (elution with 25% ethyl acetate-hexane) provided 1-4 (0.055 g) as a yellow oil. Mass spectrum (ESI): calcd for $C_{20}H_{22}N_2O_4$: 354.16; Found: 355 ($M^+$+1).

Step D

Ester 1-4 (0.055 g, 0.155 mmol) was dissolved in 1.8 mL of methanol, and then 1N NaOH solution (0.8 mL, 0.80 mmol) was added. The mixture was stirred at room temperature for 24 h, and then concentrated. The residue was dissolved in water and then cooled at 0° C. in an ice-water bath. The pH was adjusted to pH=2 using 1 N HCl solution, and then diluted with ethyl acetate. The layers were separated and the aqueous phase was extracted twice with ethyl acetate. The combined organic phases were washed with brine, dried over $Na_2SO_4$, filtered, and concentrated to give 1-5 (0.046 g) as a thick yellow oil. Mass spectrum (ESI): calcd for $C_{19}H_{20}N_2O_4$: 340.14; Found: 341 ($M^+$+1).

Step E

Amine salt 1-6 (0.107 mmol) (freshly prepared from the Boc-protected amine via standard $TFA/CH_2Cl_2$ conditions; for the preparation of this intermediate, see U.S. Pat. No. 5,536,716) was dissolved in 1.0 mL of methylene chloride, and then acid 1-5 (0.040 g, 0.118 mmol) was added. The mixture was cooled at 0° C. in and ice-water bath, and then NMM (0.50 mL, 4.5 mmol), HOBt (0.016 g, 0.118 mmol), and EDC.HCl (0.023 g, 0.118 mmol) were added. The resulting mixture was stirred at room temperature for 24 h, and then diluted with methylene chloride and washed twice with 1N HCl solution, saturated $NaHCO_3$ solution, water, and saturated NaCl solution. The organic phase was then dried over $Na_2SO_4$, filtered, and concentrated to give a yellow oil. The crude product was purified by column chromatography (3:1 methylene chloride-acetone) to give 1-7 (0.074 g) as a yellow solid. Mass spectrum (ESI): calcd for $C_{41}H_{44}ClN_5O_6S$: 769.27; Found: 770 ($M^+$+1).

Step F

Compound 1-7 (0.074 g, 0.096 mmol) was dissolved in 0.4 mL of ethyl acetate and then 0.06 mL of a solution of 30% HBr in acetic acid was added. The mixture was stirred at room temperature for 35 min whereupon a precipitate formed, and then diluted with $Et_2O$ and filtered under nitrogen to give 0.063 g of a light orange powder. HPLC analysis indicated the presence of starting material; therefore, the solid was re-subjected to the same reaction conditions. The reaction was monitored by TLC and stirred at room temperature for 45 min. The reaction mixture was diluted with Et$_2$O and the precipitate filtered under nitrogen to give 1-8 (0.038 g) as a light orange powder.

$^1$H NMR (500 MHz, CD$_3$OD) δ 8.99–8.84 (m, 1 H), 7.54–6.91 (m, 13 H), 5.21 (m, 1 H), 4.47 (m, 1 H), 4.21–4.03 (m, 2 H), 3.93–3.81 (m, 3 H), 3.70–3.65 (m, 1 H) 355–3.47 (m, 1 H), 3.34–3.29 (m, 2 H), 3.26–2.68 (m, 9 H), 1.86–1.40 (m, 3 H), 1.18–0.8 (m, 1 H); Mass spectrum (ESI): calcd for C$_{33}$H$_{38}$ClN$_5$O$_4$S: 635.23; Found: 636.5 (M$^+$+1).

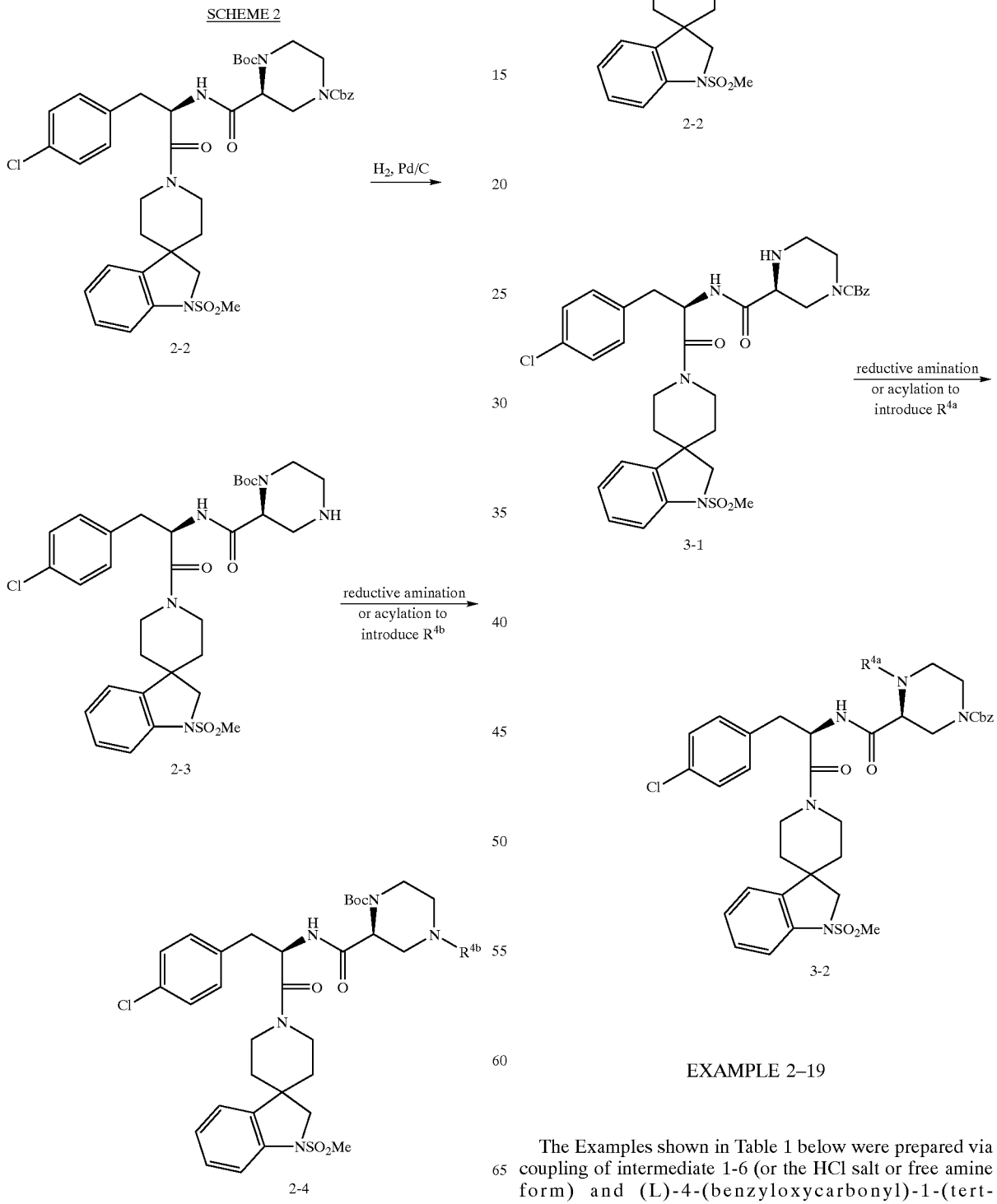

EXAMPLE 2–19

The Examples shown in Table 1 below were prepared via coupling of intermediate 1-6 (or the HCl salt or free amine form) and (L)-4-(benzyloxycarbonyl)-1-(tert-butoxycarbonyl)piperazine-2-carboxylic acid (the preparation of this intermediate from commercially available (S)-piperazine-2-carboxylic acid was achieved via modifications to the procedures described by Bigge and coworkers in *Tetrahedron Lett.* 1989, 30, 5193, namely, using $CuCl_2$ to selectively protect the β-nitrogen with CbzCl, removing the Cu coordinating group with $H_2S$ and HCl in water, and then standard Boc-protection conditions) using the procedure described in Step E of Example 1 to afford 2-2. Deprotection of the N-benzyloxycarbonyl substituent was effected by hydrogenation over Pd/C, and amine substitution with $R^{4b}$ was achieved by EDC-mediated peptide coupling with an appropriate acid in the presence of HOBt and NMM, or reductive amination of a suitable ketone or aldehyde with $NaCNBH_3$, or acylation with a suitable reagent with either triethylamine or diisopropylethylamine as base and methylene chloride or DMF as solvent. Examples of general structural formula 2-4 were obtained in this fashion and are shown in Table 1 below.

Alternatively, deprotection of the N-tert-butoxycarbonyl substituent was effected with trifluoroacetic acid in methylene chloride, and amine substitution with $R^{4a}$ was achieved by reductive amination of a suitable ketone or aldehyde with $NaCNBH_3$, or acylation with a suitable reagent with either triethylamine or diisopropylethylamine as base and methylene chloride or DMF as solvent. Examples of general structural formula 3-2 were obtained in this fashion and are shown in Table 1 below.

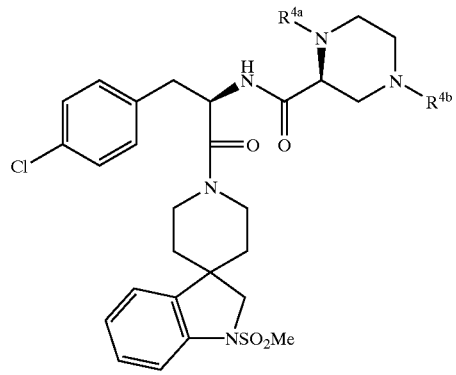

TABLE 1

| Ex. | $R^{4a}$ | $R^{4b}$ | Exact Mass | MS (ESI) |
|---|---|---|---|---|
| 2 | Boc | Cbz | 793.29 | 811($M^+$ + $NH_4^+$) |
| 3 | Boc | H | 659.25 | 660($M^+$ + 1) |
| 4 | Boc | —C(O)—C(CH3)2—NHBoc | 844.36 | 862($M^+$ + $NH_4^+$) |
| 5 | Boc | —C(O)CH3 | 701.26 | 702($M^+$ + 1) |
| 6 | Boc | cyclopropyl | 713.30 | 714($M^+$ + 1) |
| 7 | Boc | —C(=NH)NH2 | 701.28 | 702($M^+$ + 1) |
| 8 | Boc | —CH2—C6H4—OMe | 779.31 | 780($M^+$ + 1) |
| 9 | Boc | —CH2—C6H4—CF3 | 817.29 | 818($M^+$ + 1) |
| 10 | Boc | —CH2CH2OH | 703.28 | 704($M^+$ + 1) |

TABLE 1-continued

| Ex. | R⁴ᵃ | R⁴ᵇ | Exact Mass | MS (ESI) |
|-----|-----|-----|------------|----------|
| 11 | Boc | isopropyl | 673.27 | 674(M⁺ + 1) |
| 12 | Boc | sec-butyl | 687.29 | 688(M⁺ + 1) |
| 13 | Boc | isobutyl | 715.32 | 716(M⁺ + 1) |
| 14 | Boc | propionyl | 715.28 | 716(M⁺ + 1) |
| 15 | Boc | isobutyryl | 729.30 | 730(M⁺ + 1) |
| 16 | Boc | cyclopropanecarbonyl | 727.28 | 728(M⁺ + 1) |
| 17 | cyclopropylmethyl | Cbz | 747.29 | 748(M⁺ + 1) |
| 18 | acetyl | Cbz | 735.25 | 736(M⁺ + 1) |
| 19 | N-ethylcarbamoyl | Cbz | 764.28 | 765(M⁺ + 1) |

EXAMPLES 20–39

The examples illustrated in Table 2 below, were prepared by either cleavage of the N-tert-butoxycarbonyl substituent in compounds of structutral formula 2-4 with trifluoroacetic acid in methylene chloride to give the corresponding trifluoroacetic acid salts, or removal of the N-benzyloxycarbonyl substituent in compounds of structural formula 3-2 with HBr in acetic acid to give the corresponding HBr salts.

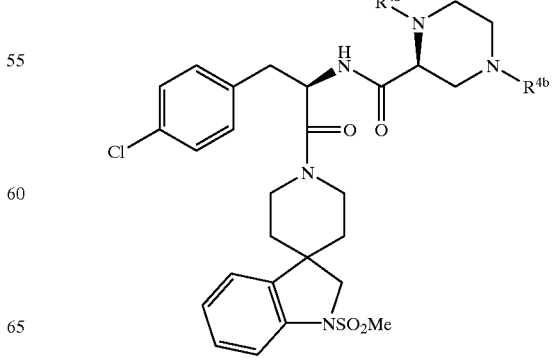

TABLE 2
| Ex. | R⁴ᵃ | R⁴ᵇ | Exact Mass | MS(ESI) |
|---|---|---|---|---|
| 20 | H | SO$_2$Me | 637.18 | 638(M⁺ + 1) |
| 21 | H | SO$_2$N(Me)$_2$ | 666.21 | 667(M⁺ + 1) |
| 22 | H | 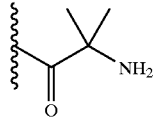 | 644.25 | 645(M⁺ + 1) |
| 23 | H | 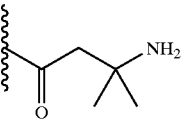 | 659.27 | 659(M⁺ + 18) |
| 24 | H | 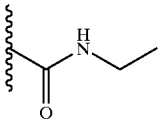 | 630.24 | 631(M⁺ + 1) |
| 25 | H | 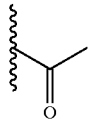 | 601.21 | 602(M⁺ + 1) |
| 26 | H | 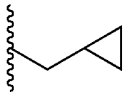 | 613.25 | 614(M⁺ + 1) |
| 27 | H | 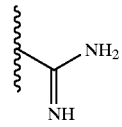 | 601.22 | 602(M⁺ + 1) |
| 28 | H | 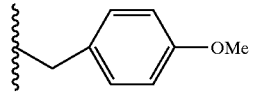 | 679.26 | 680(M⁺ + 1) |
| 29 | H | 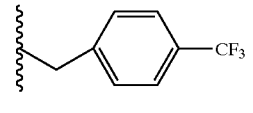 | 717.24 | 718(M⁺ + 1) |
| 30 | H | 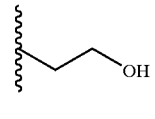 | 603.23 | 604(M⁺ + 1) |
| 31 | H |  | 573.22 | 574(M⁺ + 1) |
| 32 | H | 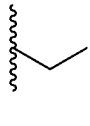 | 587.23 | 588(M⁺ + 1) |
| 33 | H | 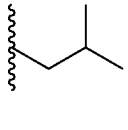 | 615.26 | 616(M⁺ + 1) |

TABLE 2-continued

| Ex. | R$^{4a}$ | R$^{4b}$ | Exact Mass | MS(ESI) |
|---|---|---|---|---|
| 34 | H | -C(=O)-CH$_2$CH$_3$ | 615.23 | 616(M$^+$ + 1) |
| 35 | H | -C(=O)-CH(CH$_3$)$_2$ | 629.24 | 630(M$^+$ + 1) |
| 36 | H | -C(=O)-cyclopropyl | 627.23 | 628(M$^+$ + 1) |
| 37 | -CH$_2$-cyclopropyl | H | 613.25 | 614(M$^+$ + 1) |
| 38 | -C(=O)-CH$_3$ | H | 601.21 | 602(M$^+$ + 1) |
| 39 | -C(=O)-NH-CH$_2$CH$_3$ | H | 630.24 | 631(M$^+$ + 1) |

BIOLOGICAL ASSAYS

A. Binding Assay

The membrane binding assay was used to identify competitive inhibitors of $^{125}$I-NDP-alpha-MSH binding to cloned human MCRs expressed in L- or CHO-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BRI); 100 ml 10% heat-inactivated fetal bovine serum (Sigma); 10 ml 10,000 unit/ml penicillin & 10,000 ug/ml streptomycin (Gibco/BRl); 10 ml 200 mM L-glutamine (Gibco/BRl); 1 mg/ml Geneticin (G418) (Gibco/BRl). The cells were grown at 37° C. with CO$_2$ and humidity control until the desired cell density and cell number was obtained.

The medium was poured off and 10 mls/monolayer of enzyme-free dissociation media (Specialty Media Inc.) was added. The cells were incubated at 37° C. for 10 minutes or until cells sloughed off when flask was banged against hand.

The cells were harvested into 200 ml centrifuge tubes and spun at 1000 rpm, 4° C., for 10 min. The supernatant was discarded and the cells were resuspended in 5 mls/ monolayer membrane preparation buffer having the composition: 10 mM Tris pH 7.2–7.4; 4 ug/ml Leupeptin (Sigma); 10 uM Phosphoramidon (Boehringer Mannheim); 40 ug/ml Bacitracin (Sigma); 5 ug/ml Aprotinin (Sigma); 10 mM Pefabloc (Boehringer Mannheim). The cells were homogenized with motor-driven dounce (Talboy setting 40), using 10 strokes and the homogenate centrifuged at 6,000 rpm, 4° C., for 15 minutes.

The pellets were resuspended in 0.2 mls/monolayer membrane prep buffer and aliquots were placed in tubes (500–1000 ul/tube) and quick frozen in liquid nitrogen and then stored at −80° C.

Test compounds or unlabelled NDP-α-MSH was added to 100 μL of membrane binding buffer to a final concentration of 1 μM. The membrane binding buffer had the composition: 50 mM Tris pH 7.2; 2 mM CaCl2; 1 mM MgCl2; 5 mM KCl; 0.2% BSA; 4 ug/ml Leupeptin (SIGMA); 10 uM Phosphoramidon (Boehringer Mannheim); 40 ug/ml Bacitracin (SIGMA); 5 ug/ml Aprotinin (SIGMA); and 10 mM Pefabloc (Boehringer Mannheim). One hundred μl of membrane binding buffer containing 10–40 ug membrane protein was added, followed by 100 μM 125I-NDP-α-MSH to final concentration of 100 pM. The resulting mixture was vortexed briefly and incubated for 90–120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 ml per well) with room temperature of filter wash having the composition: 50 mM Tris-HCl pH 7.2 and 20 mM NaCl. The filter was dried, and the bottom sealed and 50 ul of Packard Microscint-20 was added to each well. The top was sealed and the radioactivity quantitated in a Packard Topcount Microplate Scintillation counter.

B. Functional Assay

Functional cell based assays were developed to discriminate melanocortin receptor agonists from antagonists.

Cells (for example, CHO- or L-cells or other eukaryotic cells) expressing a human melanocortin receptor (see e.g. Yang-Y K; Ollmann-M M; Wilson-B D; Dickinson-C; Yamada-T; Barsh-G S; Gantz-I; Mol-Endocrinol. 1997 Mar; 11(3): 274–80) were dissociated from tissue culture flasks by rinsing with Ca and Mg free phosphate buffered saline (14190–136, Life Technologies, Gaithersburg, Md.) and detached following 5 minutes incubation at 37° C. with enzyme free dissociation buffer (S-014-B, Specialty Media, Lavellette, N.J.). Cells were collected by centrifugation and resuspended in Earle's Balanced Salt Solution (14015–069, Life Technologies, Gaithersburg, Md.) with additions of 10 mM HEPES pH 7.5, 5 mM $MgCl_2$, 1 mM glutamine and 1 mg/ml bovine serum albumin. Cells were counted and diluted to 1 to $5\times10^6$/ml. The phosphodiesterase inhibitor 3-isobutyl-1-methylxanthine was added to cells to 0.6 mM.

Test compounds were diluted in dimethylsulfoxide (DMSO) ($10^{-5}$ to $10^{-10}$ M) and 0.1 volume of compound solution was added to 0.9 volumes of cell suspension; the final DMSO concentration was 1%. After room temperature incubation for 45 min., cells were lysed by incubation at 100° C. for 5 min. to release accumulated cAMP.

cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH which was defined as a 100% agonist. The $EC_{50}$ is defined as the compound concentration which results in half maximal stimulation, when compared to its own maximal level of stimulation.

Antagonist Assay

Antagonist activity was defined as the ability of a compound to block cAMP production in response to alpha-MSH. Solution of test compounds and suspension of receptor containing cells were prepared and mixed as described above; the mixture was incubated for 15 min., and an EC50 dose (approximately 10 nM alpha-MSH) was added to the cells. The assay was terminated at 45 min. and cAMP quantitated as above. Percent inhibition was determined by comparing the amount of cAMP produced in the presence to that produced in the absence of test compound.

C. In vivo Food Intake Models

1) Overnight Food Intake

Sprague Dawley rats are injected intracerebroventricularly with a test compound in 400 nL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 hours post compound administration is measured.

2) Food Intake in Diet Induced Obese Mice

Male C57/B16J mice maintained on a high fat diet (60% fat calories) for 6.5 months from 4 weeks of age are are dosed intraperitoneally with test compound. Food intake and body weight are measured over an eight day period. Biochemical parameters relating to obesity, including leptin, insulin, triglyceride, free fatty acid, cholesterol and serum glucose levels are determined.

D. Rat Ex Copula Assay

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests

This conditioning takes ~4 days. Day 1, the animals are placed in a darkened restrainer and left for 15–30 minutes. Day 2, the animals are restrained in a supine position in the restrainer for 15–30 minutes. Day 3, the animals are restrained in the supine position with the penile sheath retracted for 15–30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation animals are given a treat to ensure positive reinforcement.

2) Ex Copula Reflex Tests

Rats are gently restrained in a supine position with their anterior torso placed inside a cylinder of adequate size to allow for normal head and paw grooming. For a 400–500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copula genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and or vehicle evaluations are conducted to determine how and if an animal will respond. Some animals have a long duration until the first response while others are non-responders altogether. During this baseline evaluation latency to first response, number and type of responses are recorded. The testing time frame is 15 minutes after the first response.

After a minimum of 1 day between evaluations, these same animals are administered the test compound at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunction

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna K E et al, *A Model For The Study of Sexual Function In Anesthetized Male And Female Rats*, Am. J. Physiol. (Regulatory Integrative Comp. Physiol 30): R1276–R1285, 1991; McKenna K E et al, *Modulation*

*By Peripheral Serotonin of The Threshold For Sexual Reflexes In Female Rats*, Pharm. Bioch. Behav., 40:151–156, 1991; and Takahashi L K et al, *Dual Estradiol Action In The Diencephalon And The Regulation Of Sociosexual Behavior In Female Golden Hamsters*, Brain Res., 359:194–207, 1985.

EXAMPLES OF A PHARMACEUTICAL COMPOSITION

As a specific embodiment of an oral composition of a composition of the present invention, 5 mg of Example 2 is formulated with sufficient finely divided lactose to provide a total amount of 580 to 590 mg to fill a size O hard gelatin capsule.

As another specific embodiment of an oral composition of a compound of the present invention, 2.5 mg of Example 2 is formulated with sufficient finely divided lactose to provide a total amount of 580 to 590 mg to fill a size O hard gelatin capsule.

Representative compounds of the present invention were tested and found to bind to the melanocortin-4 receptor. These compounds were generally found to have $IC_{50}$ values less than 2 μM. Representative compounds of the present invention were also tested in the functional assay and found generally to activate the melanocortin-4 receptor with EC50 values less than 1 μM.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for obesity, diabetes, or sexual dysfunction or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound having structural formula Ia:

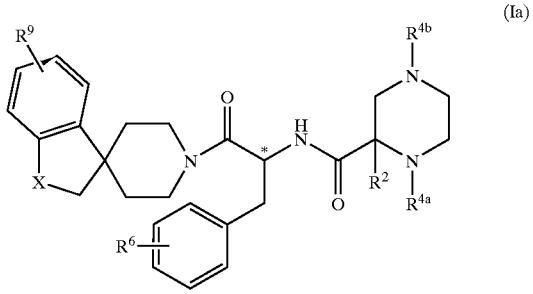

(Ia)

wherein
n is 0, 1, or 2;
X is $N\text{-}SO_2R^8$;

$R^6$ is hydrogen, halo, or methoxy;
$R^2$ is hydrogen or methyl;
$R^9$ is hydrogen or halo;
$R^{4a}$ and $R^{4b}$ are each independently selected from the group consisting of
hydrogen,
amidino,
$C_{1-4}$ alkyl,
$(CH_2)_{0-1}$ aryl,
$(CH_2)_{0-1}C_{3-6}$ cycloalkyl,
$CO_2R^7$,
$CO(CH_2)_{0-1}C(Me)_2NH_2$,
$COC(Me)_2NHCO_2R^7$,
$(CH_2)_2OR^7$,
$COR^7$,
$CONR^7R^7$,
$SO_2R^7$, and
$SO_2NR^7R^7$;
in which aryl is unsubstituted or substituted with one to three groups independently selected from $R^6$; and alkyl and cycloalkyl are unsubstituted or substituted with one to three groups independently selected from $R^6$ and oxo;
each $R^7$ is independently selected from the group consisting of
hydrogen,
$C_{1-8}$ alkyl,
$(CH_2)_n$-aryl, and
$(CH_2)_nC_{3-7}$ cycloalkyl; and
$R^8$ is selected from the group consisting of
hydrogen,
$C_{1-8}$ alkyl,
$(CH_2)_n$-aryl, and
$(CH_2)_nC_{3-7}$ cycloalkyl;
wherein aryl is unsubstituted or substituted with one to three groups independently selected from $R^6$; and alkyl, cycloalkyl, and $(CH_2)_n$ are unsubstituted or substituted with one to three groups independently selected from $R^6$ and oxo;

or a pharmaceutically acceptable salt thereof.

2. The compound of claim 1 wherein $R^{4a}$ and $R^{4b}$ are each independently selected from the group consisting of
hydrogen,
$C_{1-4}$ alkyl,
$(CH_2)_{0-1}$ aryl, and
$(CH_2)_{0-1}C_{3-6}$ cycloalkyl;
in which aryl is unsubstituted or substituted with one to three groups independently selected from $R^6$; and alkyl and cycloalkyl are unsubstituted or substituted with one to three groups independently selected from $R^6$ and oxo.

3. The compound of claim 1 wherein the carbon atom marked with * has the R configuration.

4. The compound of claim 2 wherein the carbon atom marked with * has the R configuration.

5. The compound of claim 1 of structural formula Ic selected from the group consisting of:
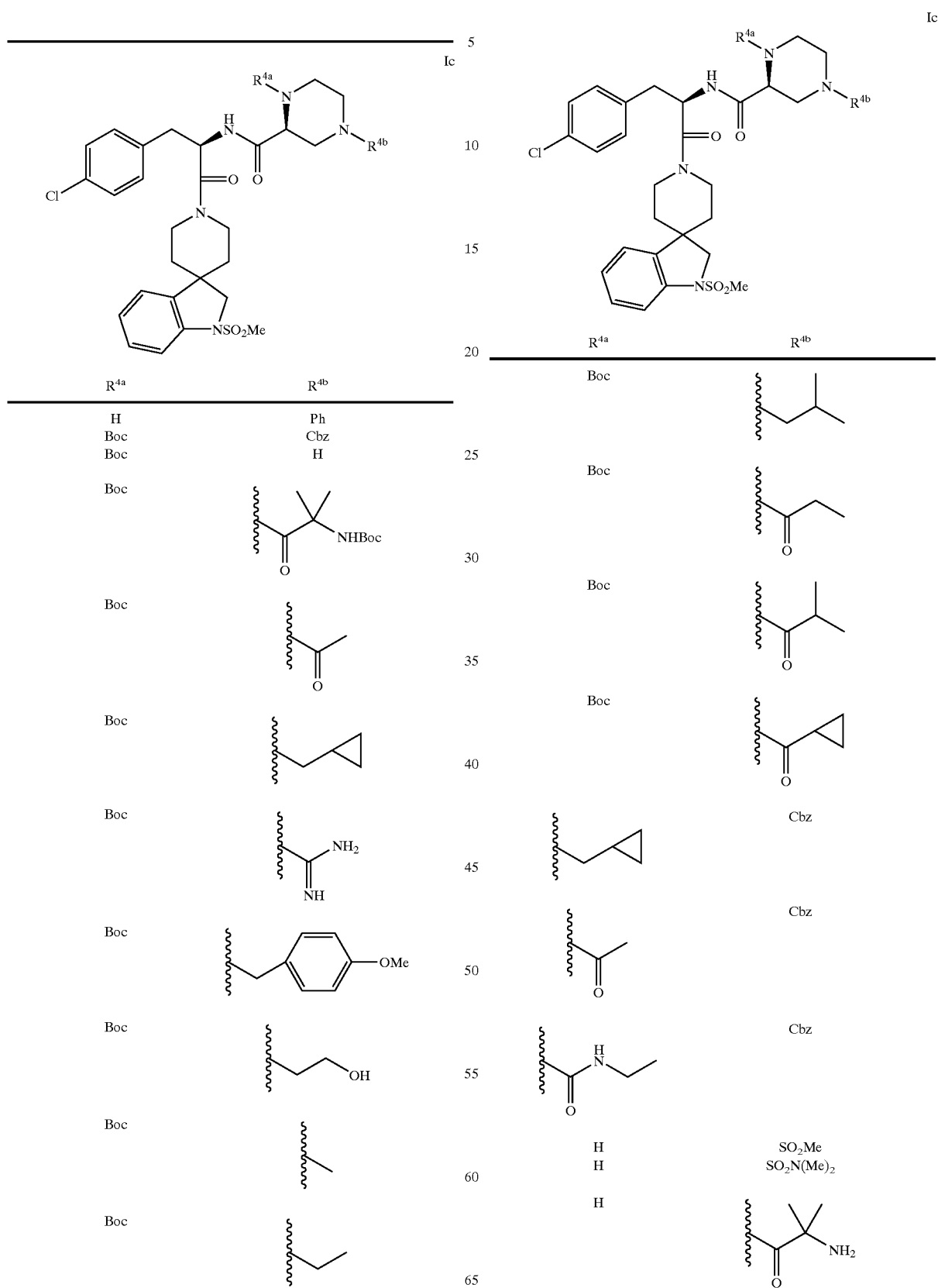

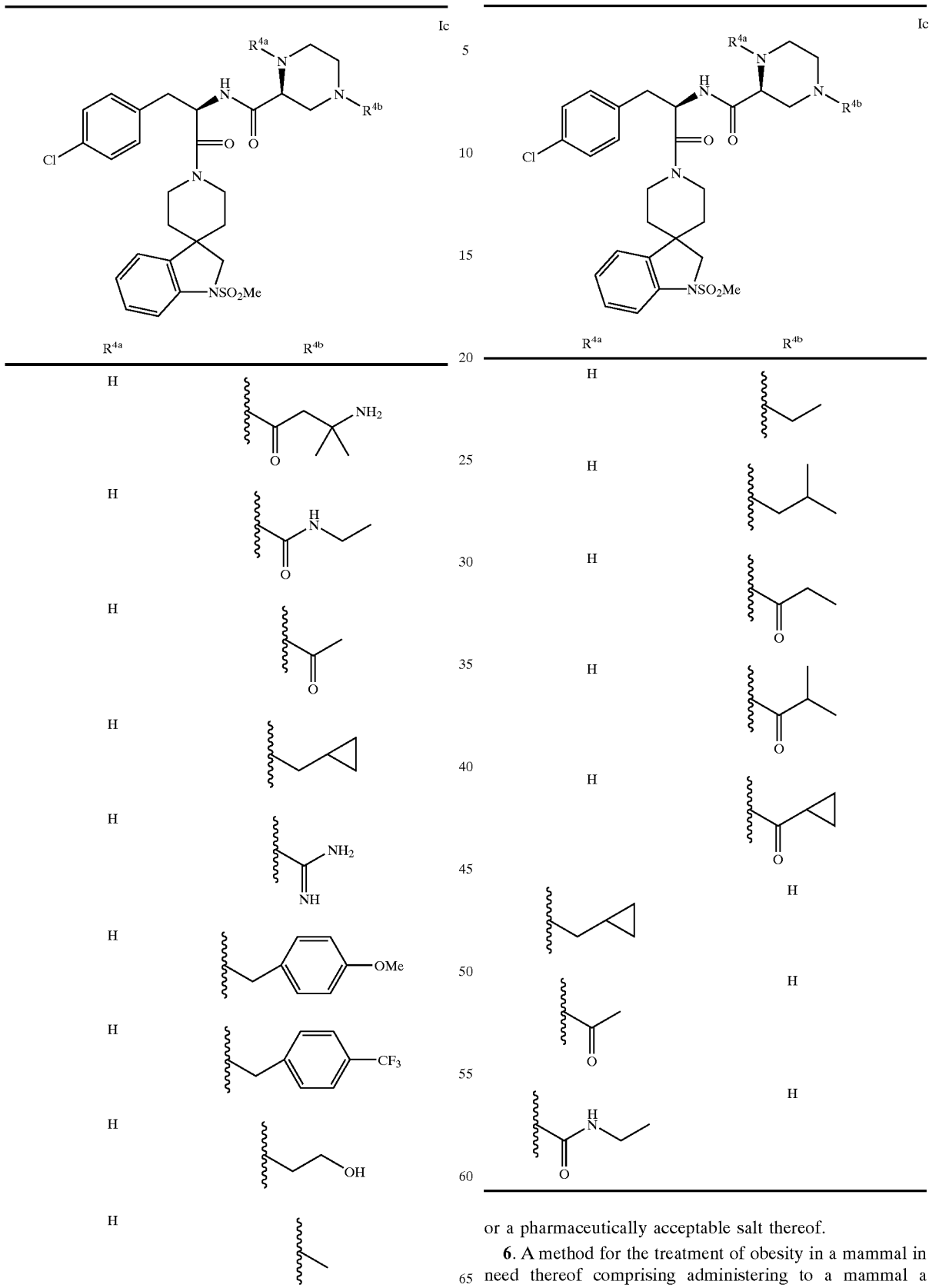
or a pharmaceutically acceptable salt thereof.
6. A method for the treatment of obesity in a mammal in need thereof comprising administering to a mammal a therapeutically effective amount of a compound according to claim 1.

7. A method for the treatment of diabetes mellitus in a mammal in need thereof comprising administering to a mammal a therapeutically effective amount of a compound according to claim 1.

8. A method for the treatment of male or female sexual dysfunction in a mammal in need thereof comprising administering to a mammal a therapeutically effective amount of a compound according to claim 1.

9. A method for the treatment of erectile dysfunction in a mammal in need thereof comprising administering to a mammal a therapeutically effective amount of a compound according to claim 1.

10. A pharmaceutical composition which comprises a compound of claim 1 and a pharmaceutically acceptable carrier.

11. A method of treating male or female sexual dysfunction in a mammal in need thereof, comprising administering to the mammal a therapeutically effective amount of the composition of claim 10.

* * * * *